United States Patent
Kramer et al.

(10) Patent No.: US 6,725,901 B1
(45) Date of Patent: Apr. 27, 2004

(54) METHODS OF MANUFACTURE OF FULLY CONSOLIDATED OR POROUS MEDICAL DEVICES

(75) Inventors: Pamela A. Kramer, San Jose, CA (US); James M. Carlson, Gilroy, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 10/330,642

(22) Filed: Dec. 27, 2002

(51) Int. Cl.[7] .............................................. B22D 17/00
(52) U.S. Cl. ........................ 164/113; 164/900; 623/901
(58) Field of Search ................................. 164/113, 900, 164/312; 623/901, 1

(56) References Cited

U.S. PATENT DOCUMENTS

| | | | |
|---|---|---|---|
| 4,694,881 A | 9/1987 | Busk ........................... | 164/113 |
| 4,694,882 A | 9/1987 | Busk ........................... | 164/113 |
| 5,037,489 A * | 8/1991 | Kirkwood et al. .......... | 148/546 |
| 5,040,589 A | 8/1991 | Bradley et al. ............. | 164/113 |
| 5,158,548 A | 10/1992 | Lau et al. ..................... | 604/96 |
| 5,421,955 A | 6/1995 | Lau et al. ..................... | 216/48 |
| 5,514,154 A | 5/1996 | Lau et al. .................... | 606/195 |
| 5,711,366 A | 1/1998 | Mihelich et al. ............ | 164/312 |
| 5,780,807 A | 7/1998 | Saunders ............... | 219/121.71 |
| 5,819,839 A | 10/1998 | Mihelich et al. ............ | 164/312 |
| 5,881,796 A | 3/1999 | Brown et al. ............... | 164/113 |
| 5,887,640 A | 3/1999 | Brown et al. ............... | 164/133 |
| 5,972,027 A * | 10/1999 | Johnson ..................... | 623/1.42 |
| 5,983,978 A | 11/1999 | Vining et al. ............... | 164/312 |
| 5,996,679 A | 12/1999 | Pinnow et al. .............. | 164/312 |
| 6,059,012 A | 5/2000 | Vining et al. ............... | 164/312 |
| 6,131,266 A | 10/2000 | Saunders ..................... | 29/557 |
| 6,136,101 A * | 10/2000 | Sugawara et al. .......... | 148/321 |
| 6,241,001 B1 * | 6/2001 | Kono .......................... | 164/312 |
| 6,299,665 B1 | 10/2001 | LeBeau et al. .............. | 75/255 |
| 6,308,768 B1 | 10/2001 | Rice et al. ................... | 164/133 |
| 6,432,133 B1 | 8/2002 | Lau et al. ................... | 623/1.15 |
| 6,527,938 B2 * | 3/2003 | Bales et al. ................. | 205/229 |
| 6,641,776 B1 * | 11/2003 | Weaver et al. .............. | 264/642 |

OTHER PUBLICATIONS

C.K. Jen, J.W. Liaw, T.F. Chen, A. Moreau, J.P. Monchalin and C.C. Yang, Ultrasonic evaluation of semi–solid metals during processing, Measurement Science and Technology, vol. 11, No. 11 (Nov. 2000), pp. 1570–1575.

D.M. Gao; A. Garcia–Rejon; R. Fan, D. Ghosh and C. Van Schilt, Numerical Modeling of Fluid Flow and Heat Transfer in Thixomolding, Advances in Powder Metallurgy and Particulate Materials, vol. 6, (1996), pp. 20–77–20–84.

Thixomolding Net–Shape Metal Parts, Advanced Materials & Processes (Nov. 2001), pp. 54–55.

Chris S. Rice and Patricio F. Mendez, Slurry–Based Semi–Solid Die Casting, Advanced Materials & Processes (Oct. 2001), pp. 49–54.

Joseph Ogando, Thixomolding, what's that?, Design News (Apr. 17, 2000), (printed from http://www.findarticles.com/cf_dis/m1068/8_55/61543488/print.jhtml on Jul. 10, 2002).

Thixotech Inc: Thixomolding, (printed from http://www.thixotech.com/thixomld.htm on Sep. 12, 2002) (Three pages).

(List continued on next page.)

*Primary Examiner*—Kuang Y. Lin
*Assistant Examiner*—I.-H. Lin
(74) *Attorney, Agent, or Firm*—Fulwider Patton Lee & Utecht, LLP (57) ABSTRACT

The invention relates to methods of manufacturing various medical devices and starting materials by utilizing the processes of high speed injection molding and slurry-based, semi-solid die casting applied to biocompatible metals or metal alloys that may have a high melting point temperature. These devices may be made fully consolidated or porous to allow the devices to act as a functional drug delivery vehicle.

4 Claims, 6 Drawing Sheets

OTHER PUBLICATIONS

Magnesium Injection Thixomolding Molding–Thixomat, Inc. Aluminum Die Cast, Frequently Asked Questions About Thixomolding, (printed from http://www.thixomat.com/th103d31.htm on Sep. 12, 2002) (2000) (Seven pages).

Magnesium Injection Thixomolding Molding–Thixomat, Inc. Aluminum Die Cast, Thixomolding Benefits, (printed from http://www.thixomat.com/th102d02.htm on Sep. 12, 2002) (2000) (Four pages).

Magnesium Injection Thixomolding Molding–Thixomat, Inc. Aluminum Die Cast, Composite Metal/Plastic Molding Technology, (printed from http://www.thixomat.com/th103d33.htm on Sep. 12, 2002) (2000) (Three pages).

Magnesium Injection Thixomolding Molding–Thixomat, Inc. Aluminum Die Cast, Thixomolding Changing the Face of Products Worldwide, (printed from http://www.thixomat.com/th103d30.htm on Sep. 12, 2002) (2000) (Three pages).

* cited by examiner

METHODS OF MANUFACTURE OF FULLY CONSOLIDATED OR POROUS MEDICAL DEVICES

BACKGROUND OF THE INVENTION

This invention relates to medical devices, and more particularly, the invention relates to methods of manufacturing various medical devices utilizing the processes of high speed injection molding and semi-solid (slurry-based) die casting applied to biocompatible metals and metal alloys that may have a high melting point temperature. These devices may be made porous to allow such devices to act as a functional drug delivery vehicle.

Several interventional treatment modalities are presently used for heart disease, including balloon and laser angioplasty, atherectomy, and bypass surgery. In typical coronary balloon angioplasty procedures, a guiding catheter having a distal tip is percutaneously introduced through the femoral artery into the cardiovascular system of a patient using a conventional Seldinger technique and advanced within the cardiovascular system until the distal tip of the guiding catheter is seated at the ostium of the coronary arteries. A guide wire is positioned within an inner lumen of a dilatation catheter and then both are advanced through the guiding catheter to the distal end thereof.

The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion.

Once in position across the lesion, the balloon is inflated to compress the plaque of the lesion against the inside of the artery wall and to otherwise expand the inner lumen of the artery. The balloon is then deflated so that blood flow can be resumed through the dilated artery and the dilatation catheter can be removed therefrom.

One problem that can occur during balloon angioplasty procedures is the formation of intimal flaps which can collapse and occlude the artery when the balloon is deflated at the end of the angioplasty procedure. Another problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices referred to as stents. Stents are generally cylindrically shaped intravascular devices which are placed within an artery to hold it open. The device can be used to reduce the likelihood of restenosis and to maintain the patency of a blood vessel immediately after intravascular treatments. In some circumstances, they can also be used as the primary treatment device where they are expanded to dilate a stenosis and then left in place.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

Certain metals and metal alloys, including those capable of being used in the manufacture of various medical devices, exhibit dendritic crystal structures at ambient temperatures. These metals and metal alloys are known as being capable of transforming into a thixotropic state upon the application of heating and shearing. The metal or metal alloy forms into a semi-solid slurry while being heated and maintained at a temperature above its solidus temperature (i.e., temperature at which a material forms into a fully solid state) and below its liquidus temperature (i.e., temperature at which a material forms into a fully liquid state). In order to inhibit the formation of dendritic shaped (i.e., tree-like structure) solid particles in the semi-solid slurry, shearing is applied to and maintained in the slurry mixture. Accordingly, this vigorous shearing action results in the formation of primary solids containing discrete, degenerate dendrites or nodules. The remaining unsolidified liquid alloy of the semi-solid slurry surrounds the degenerate dendrites or nodules. It is this combination of materials that results in the semi-solid slurry being in a thixotropic state.

Various apparatuses for processing thixotropic materials, particularly magnesium and aluminum based alloys, are known in the metallurgical art. Such apparatuses typically include a reciprocating extruder having a barrel that is coupled to a mold (see FIGS. 1 and 2). The extruder barrel has inlet and outlet ends at opposite ends of the apparatus. The inlet end is adapted to receive the metallic material from a solid particulate, pelletized or liquid metal feeder. Depending on the condition of the metallic material as it is being received into the extruder barrel, heating elements either increase the temperature of the metallic material or maintain the material at a predetermined temperature in order for the material to be brought into the two phase solidus-liquidus region. The material is formed into an equilibrium state having both solid and liquid phases while in the extruder barrel. A reciprocating screw positioned in the barrel applies a shearing action to the thixotropic or semi-solid slurry material. The thixotropic material is then ready to be transformed into a mold, and thereafter removed once it has solidified into its net shape.

The processes of high speed injection molding and semi-solid (slurry-based) die casting are primarily used in automotive, consumer electronics, and consumer hardware applications. However, there exists a need to apply these processes in the context of medical device applications using certain biocompatible materials in their thixotropic state to form various types of medical devices. The present invention meets these and other needs.

SUMMARY OF THE INVENTION

The present invention is directed to methods of manufacturing various types of medical devices utilizing either one of the processes of high speed injection molding or semi-solid (slurry-based) die casting applied to biocompatible metals and metal alloys that may have a high melting point temperature. The processes are further expanded to include the manufacture of porous tubing or devices for use as drug-eluting medical devices, such as stents.

In view of the foregoing, it is apparent that there still exists a need in the metallurgical art for methods of manufacturing various biomedical devices using known and to be developed biocompatible metals and metal alloys in their thixotropic semi-solid state in combination with one of the processes of high speed injection molding and semi-solid (slurry-based) die casting. Accordingly, the processes of high speed injection molding and semi-solid die casting when applied to a select group of biocompatible metals or metal alloys that may have a high melting point temperature provide methods of manufacturing various medical devices and performs, such as stents, stent tubing (e.g., both straight-walled and variable thickness), endovascular grafts, pacemaker leads, anastomosis clips and anastomosis clip tubing, among others. Manufacture of longer lengths of variable thickness tubing would cut down on the amount of waste seen with today's manufacturing methods of this type of tubing. Further, in consideration of the development of thin radiopaque novel alloys having magnetic resonance imaging (MRI) compatibility, these processes may allow easier manufacture of such new materials. These processes could be expanded to include the manufacture of porous tubing or devices for use as drug-eluting stents.

One aspect of the present invention involves a method of making a medical device. The method includes providing a biocompatible material, and forming a medical device therefrom utilizing a high speed injection molding process. The material can be a biocompatible metal or metal alloy that may have a high melting point temperature. Exemplary of alloy families that may be used as the biocompatible materials include iron-carbon, cobalt based superalloys, cobalt-chromium, tantalum, titanium, nitinol, niobium, niobium-vanadium, niobium-zirconium, niobium-tantalum-zirconium, titanium-tantalum, tantalum-titanium, niobium-tantalum, tantalum-niobium, niobium-titanium, titanium-niobium, tantalum-tungsten, tantalum-tungsten-hafnium, palladium-silver, silver-palladium, and platinum-iridium. An example of a medical device that can be formed in accordance with the high speed injection molding process includes configuring a stent-having a plurality of connected cylindrical rings.

The high speed injection molding process further includes processing the biocompatible material into a semi-solid thixotropic state while being maintained in a thermally controlled chamber. The biocompatible material is processed into the semi-solid thixotropic state by being heated to a temperature above its solidus temperature and below its liquidus temperature. Since the present invention employs the use of certain biocompatible metals or metal alloys that may have a high melting point temperature, the thermally controlled chamber can be modified to have a higher heating capacity by being fabricated from materials that are capable of accommodating these higher temperature requirements. The heating capacity of the thermally controlled chamber is generally dependent on the particular biocompatible material selected. A shearing action is then applied to the semi-solid thixotropic substrate in the thermally controlled chamber. This shearing action can be by mechanical or electromagnetic means. The semi-solid thixotropic material is injection molded at a high speed into a die. The co-injection of dispersoids such as ceramic or oxide into the injection molded thixotropic material can be used to influence the mechanical properties of the substrate. The die can be fabricated from a less heat resistant material that is thermally sprayed or dip coated with a heat resistant material that acts as a thermal barrier and maintains the integrity of the die. Alternatively, the die can be fabricated entirely from heat resisting materials. The injection molded thixotropic material begins to solidify as it cools. After the material sufficiently cools, it can be removed from the die. Appropriate post-processing steps can be applied to the medical device or perform for further completion of the device.

Another aspect of the present invention involves a method of making a porous medical device utilizing the high speed injection molding process. One way to make the device porous is to mix a binder with the biocompatible material while being maintained in the thixotropic state and then inject the mixture into the die. An additional post-processing step can be applied to the medical device for removal of the binder material, e.g., by dissolving in an appropriate solvent or by baking the part to sublimate or vaporize the binder material. After removal of the binder material, the medical device is ready for impregnation with a drug, such as antiplatelets, anticoagulants, antifibrins, antithrombins, and antiproliferatives. For purposes of this invention, the term "impregnate" means to fill throughout or saturate.

In a further aspect of the present invention, a method of making a medical device utilizing the process of semi-solid (slurry-based) die casting is disclosed. The method includes providing a biocompatible material and forming a medical device. Semi-solid die casting is similar to the process of high speed injection molding as set forth above. The biocompatible material is processed into a semi-solid slurry suspension wherein the biocompatible material is heated to a temperature above its solidus temperature and below its liquidus temperature while in a thermally controlled chamber. A shearing force is simultaneously applied to the semi-solid slurry suspension while being maintained in a semi-solid slurry suspension. After being transferred to the die casting device while being maintained in a thermally controlled environment, the semi-solid suspension is die cast into form at a high temperature. The semi-solid suspension solidifies as it cools, after which time the medical device can be removed from the die. The medical device can be made porous for subsequent impregnation with a drug by mixing a binder into the biocompatible material, while being maintained in a semi-solid suspension, and then casting the mixture into the die.

The present invention also involves methods of making tube stock. In particular, the methods include providing a biocompatible material and forming tube stock using one of the processes of high speed injection molding or semi-solid die casting. Exemplary medical devices that can be formed in accordance with the present invention include an intravascular device, a stent, an embolic protection device, an attachment system for an endovascular graft, a guide wire, a wire lead, a catheter, a pacemaker lead end, and an anastomosis device.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention relates to manufacturing processes utilizing biocompatible metals and metal alloys for forming medical devices. The present invention includes methods of making medical devices by using processes including high speed injection molding or semi-solid (slurry-based) die casting being applied to a particular biocompatible metal and metal alloy that may have a high melting point temperature. While virtually any medical device that is implanted or used in the body will benefit from the present invention, the invention as applied to stents is described herein as only an example and is not meant to be limiting. Thus, medical devices made by the processes of the present invention include, but are not limited to, stents, guide wires, embolic protection filters, markers, defibrillator and pace maker leads, endovascular grafts, mitral valves and anastomosis devices. The method of the present invention may be used to manufacture near net shape devices or starting materials, such as tube stock, wire, and metal sheets. Further, the processes of the present invention may be adapted for the manufacture of drug-eluting stents and other medical devices.

Figure 1:
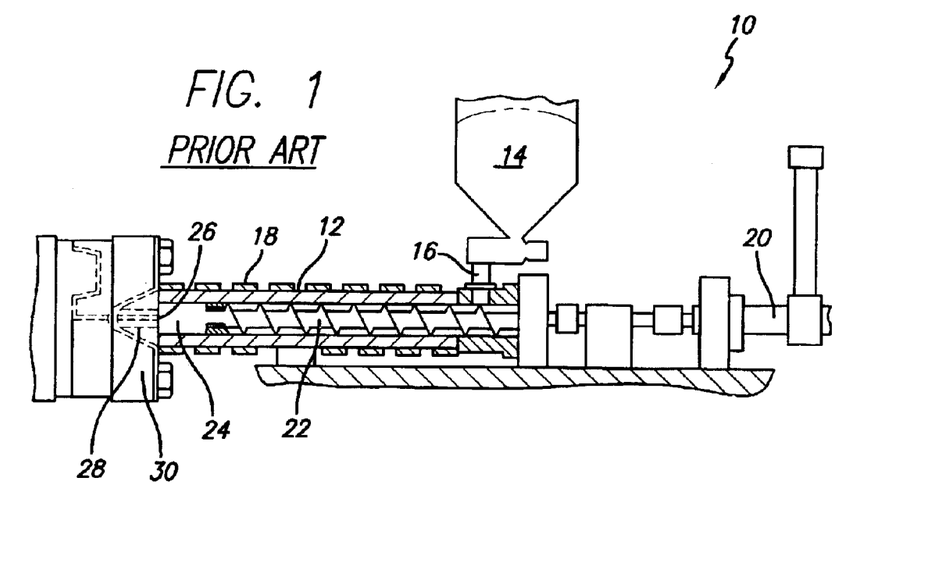
FIG. 1 is a schematic illustration of a prior art apparatus for high speed injection of magnesium based alloys into a thixotropic state for subsequent fabrication into an article.
Figure 2:
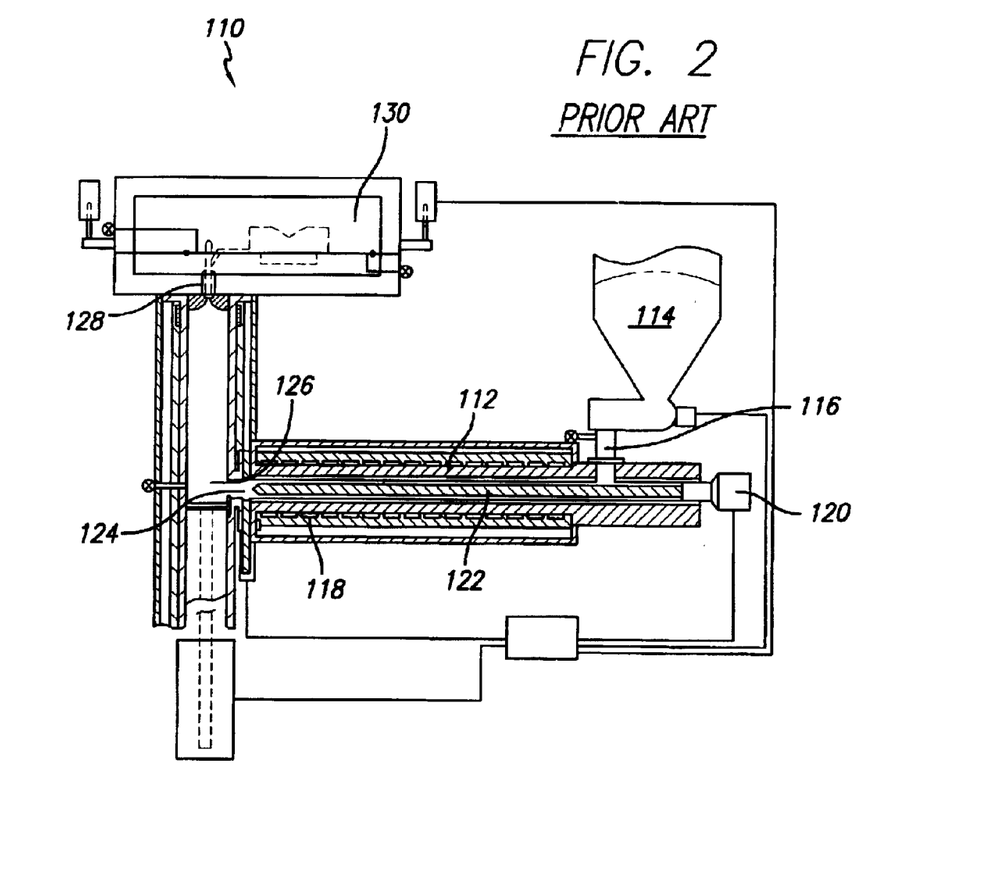
FIG. 2 is a schematic illustration of a prior art apparatus for semi-solid die casting of aluminum based alloys into a thixotropic state for subsequent fabrication into an article.

Heretofore, the metallurgical arts have taught methods and apparatuses for high speed injection of magnesium based alloys in a thixotropic state or semi-solid slurry suspension for subsequent fabrication into an article of manufacture (FIG. 1). Similarly, the art has provided methods and apparatuses for die casting aluminum based alloys in a thixotropic state or semi-solid slurry suspension for subsequent fabrication into an article of manufacture (FIG. 2). The terms "thixotropic state" and "semi-solid slurry suspension" are used interchangeably herein, as both terms refer to a mixture of a liquid and solid phase consisting of rounded solid phase particles suspended, in a liquid matrix. As set forth herein, in forming a medical device or tube stock using the processes of high speed injection molding and semi-solid die casting, the present invention modifies the prior art apparatuses, such as those shown in FIGS. 1 and 2, to have the capability to accommodate the use of metals or metal alloys that have a relatively high melting point temperature in comparison to previously used materials.

With further reference to FIGS. 1 and 2, known prior art apparatuses 10, 110 used in the processing of aluminium and magnesium based metals and metal alloys in a thixotropic state for the manufacture of net shape parts generally include a barrel 12, 112 and a feeder 14, 114 in which the barrel is adapted to receive the metallic material from the feeder through an inlet 16, 116 positioned proximate a first (inlet) end of the barrel. The material is generally received in a solid form, such as pellet, chip, flake, powder or the like, or in a molten form, such as liquid or semi-liquid. Depending on the form of material that is received into the barrel, heating elements 18, 118 either heat the metallic material or maintain it at a predetermined temperature in order to attain the two phase solidus-liquidus region for such material. Accordingly, since the temperature of the material in the barrel is between the solidus and liquidus temperatures in this region, it can be said that the material is in a thermodynamic equilibrium state, having both solid and liquid phases.

Positioned in the barrel 12, 112 and rotated by an actuator 20, 120 is a reciprocating screw 22, 122 that moves the material through the barrel while applying a shearing action to the material. It is this shearing action that conditions the material into a semi-solid slurry having solid degenerate dendritic structures surrounded by the material in a liquid phase. Following the collection of an appropriate amount of material at a second (exit) end 24, 124 of the barrel, the reciprocating screw is rapidly rotated, thereby moving the material through an outlet 26, 126 of the barrel, then through a nozzle 28, 128 and finally into a mold or die 30, 130. In the die, the material solidifies as it cools and the newly formed injection molded part may be removed from the die.

The present invention includes a process of manufacturing a medical device by first providing a suitable biocompatible material to form the body of the medical device. The biocompatible material may be derived from a metal or metal alloy. Examples of various metals and metal alloys that can be used in accordance with the present invention include, but are not limited to, iron-carbon, cobalt based superalloys, cobalt-chromium, tantalum, titanium, nickel-titanium, niobium, niobium-vanadium, niobium-zirconium, niobium-tantalum-zirconium, titanium-tantalum, tantalum-titanium, niobium-tantalum, tantalum-niobium, niobium-titanium, titanium-niobium, tantalum-tungsten, tantalum-tungsten-hafnium, palladium-silver, silver-palladium, and platinum-iridium. Each of these particular types of metals and metal alloys tends to possess a high melting point temperature (see Table 1). The suitable biocompatible material may have a melting point temperature from about 2000° Fahrenheit (F) to about 5700° F. The process of high speed injection molding or semi-solid die casting is then applied to the biocompatible material to form a net shape medical device, wire, tube stock, or the like. Appropriate post-processing can be applied to the medical device as needed and is described in further detail below.

As set forth below in Table 1, each metal or metal alloy that can be used in accordance with the present invention is listed with its respective melting point temperature:

TABLE 1

Melting Temperatures For Various Alloy Systems

| Alloy Family | Specific Alloy (weight percent) [ASTM SPEC] | Melting temperature (Fahrenheit) | Melting temperature (Celsius) |
|---|---|---|---|
| Iron-carbon | 316L [F138] | 2510–2550 | 1377–1398 |
| Iron-carbon | 302 | 2550–2590 | 1398–1421 |
| Iron-carbon | 304 | 2550–2650 | 1398–1454 |
| Cobalt based superalloys | L-605, Haynes 25 [F90] | 2570 | 1410 |
| Cobalt based superalloys | MP-35N [F562] | 2400–2620 | 1316 |
| Cobalt based superalloys | Elgiloy [F1058] | 2600 | 1427 |
| Cobalt based superalloys | Haynes 188 | 2400–2570 | 1316–1410 |
| Tantalum | Commercially pure | 5468 | 3020 |
| Titanium | Commercially pure | 3038 | 1670 |
| Nickel-titanium | Ni - 50Ti [F2063] | 2264–2390 | 1240–1310 |
| Niobium | Commercially pure | 3470 | 1910 |
| Niobium - vanadium | Nb - 4V | 3452 | 1900 |
| Niobium - zirconium | Nb - 1Zr | 4428 | 2460 |
| Niobium - tantalum -zirconium | Nb - 10Ta - 2.5Zx | 4400 | 2425 |
| Titanium - tantalum | Ti - 20Ta | 3272 | 1800 |
| Titanium - tantalum | Ti - 40Ta | 3560 | 1960 |
| Titanium - tantalum | Ti - 50Ta | 3740 | 2060 |
| Tantalum - titanium | Ta - 40Ti | 3884 | 2140 |
| Tantalum - titanium | Ta - 20Ti | 4496 | 2480 |
| Niobium - tantalum | Nb - 20Ta | 4604 | 2540 |
| Niobium - tantalum | Nb - 40Ta | 4748 | 2540 |
| Niobium - tantalum | Nb - 50Ta | 4820 | 2660 |
| Tantalum - niobium | Ta - 40Nb | 4910 | 2710 |
| Tantalum - niobium | Ta - 20Nb | 5144 | 2840 |
| Niobium - titanium | Nb - 20Ti | 3848 | 2120 |
| Niobium - titanium | Nb - 40Ti | 3452 | 1900 |
| Niobium - titanium | Nb - 45Ti | 3416 | 1880 |
| Niobium - titanium | Nb - 50Ti | 3344 | 1840 |
| Titanium - niobium | Ti - 45Nb | 3308 | 1820 |
| Titanium - niobium | Ti - 40Nb | 3272 | 1800 |
| Titanium - niobium | Ti - 20Nb | 3128 | 1720 |
| Tantalum - tungsten | Ta - 10W | 5558 | 3070 |
| Tantalum - tungsten | Ta - 20W | 5630 | 3110 |
| Tantalum - tungsten - hafnium | Ta - 7.5W - 2.5Hf | >5000 | >2760 |
| Tantalum - tungsten - hafnium | Ta - 10W - 2.5Hf | >5000 | >2760 |
| Palladium - silver | Pd - 20Ag | 2642 | 1450 |
| Palladium - silver | Pd - 40Ag | 2516 | 1380 |
| Palladium - silver | Pd - 50Ag | 2408 | 1320 |
| Silver - palladium | Ag - 40Pd | 2300 | 1260 |
| Silver - palladium | Ag - 20Pd | 2066 | 1130 |
| Platinum - iridium | Pt - 5Ir | 3184 | 1769 |
| Platinum - iridium | Pt - 10Ir | 3272 | 1800 |
| Platinum - iridium | Pt - 15Ir | 3344 | 1840 |

During high speed injection molding, the metal or metal alloy is processed into a semi-solid thixotropic state while being maintained in a thermally controlled chamber (barrel) 12, 112 (FIGS. 1 and 2). Since certain biocompatible alloys may have a higher melting point temperature than aluminum and magnesium based materials, the thermally controlled chamber, used in the high speed injection molding process, must be able to withstand such high temperatures. Accordingly, the thermally controlled chamber of the present invention may need to be modified from the standard heating chamber used with lower melting point temperature aluminum and magnesium based alloys, such that the chamber has a higher heating capacity when such higher melting point temperature biocompatible metals and metal alloys are used.

In the present invention, the biocompatible material is heated to and maintained at a temperature that is above the material's solidus temperature and below the material's liquidus temperature, and results in the formation of a semi-solid slurry. While being maintained within the thermally controlled chamber, a shearing action is applied to the material in the semi-solid thixotropic state to prevent the formation of dendritc shaped solid particles in the semi-solid material. The shearing action may be by various known or to be determined processes, including mechanical or electromagnetic.

After the semi-solid material attains a desired level of viscosity, the semi-solid material may be injected at high velocity (e.g., 16 k/hr to 1850 kg/hr) into a die or mold 30 (FIG. 1). The parts of the die are produced to precise design criteria for shape, dimensions, and properties. As with the thermally controlled chamber, the die is another primary component of the apparatus used in conjunction with the present invention that may require modification in order to tolerate the typically higher temperature biocompatible material. Examples of various heat resistant materials that can be used in the fabrication of the die in accordance with the present invention include graphite, ceramic, high melting point temperature elements or alloys, such as lead or lead-based, tantalum or tantalum based, tungsten or tungsten based, and the like. These materials may be used with or without a liner such as graphite or a ceramic material. Alternatively, the die can be fabricated from a less heat resistant material that is either dip coated or thermally sprayed with a refractory metal or other more heat resistant material that acts as a thermal barrier and maintains the integrity of the die component.

The semi-solid thixotropic material solidifies as it cools, and cooling of the material may be enhanced by known processes. After the thixotropic material has solidified the newly formed net shape medical device is removed from the die and is ready for use, providing that additional post-processing is not necessary. The net shape medical device can be configured into a stent, which may include a plurality of connected cylindrical rings. More specifically, a machine-controlled laser may be used to cut a pattern into the stent (described in further detail below) so as to configure a stent with a plurality of connected cylindrical rings. It should be appreciated that the present invention contemplates the use of various stent designs and is not meant to be limited to solely a ring-and-link design.

Advantages of using a high speed injection molding process to manufacture medical device applications include dimensional stability, low porosity, and tighter part tolerances with reduced shrinkage, lower residual stress, and less component distortion. In addition, products useful for medical device applications can be formed to a net shape using the methods disclosed herein. The medical devices and tubing can be made porous for use as drug delivery devices.

In an alternative embodiment of the present invention, the medical device made according to the method of the present invention can be made porous for controlled release of drugs and for delivery of the drugs in localized drug therapy in a blood vessel. At the step of forming a medical device using a high speed injection molding process, a binder is injected into the semi-solid thixotropic material while the material is retained in a die so as to form pores throughout the body of the net shape medical device. Examples of binder materials that can be used in accordance with the present invention include polysilazine (i.e., silazine based polymer), unsaturated polymer resin, bisphenoic unsaturated polymer resin, thermoplastic polymer, polycarbonate, and colloidal silica. The binder is removed from the newly formed medical device through post-processing known in the art A polymer barrier coat layer can be disposed over the outer surface of the medical device to further control elution of the drug.

Various therapeutic agents, drugs and other pharmacologic compounds may be loaded into the porous medical device and delivered to the target site in the vasculature. Classes of such compounds include, but are not limited to, substances that are antiproliferative, antithrombogenic, antineoplastic, antiinflammatory, antiplatelet, anticoagulant, antifibrin, antithrombin, antimitotic, antibiotic, and antioxidant. Specific examples of therapeutic agents or drugs that are suitable for use in accordance with the present invention include taxol, paclitaxel, docetaxel, sirolimus, everolimus, actinomycin D (ActD), prostaglandins, aspirin or derivatives and analogs thereof.

Examples of antiplatelets, anticoagulants, antifibrins, and antithrombins include, but are not limited to, sodium heparin, low molecular weight heparin, hirudin, argatroban, forskol in, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E–3B (an antiplatelet drug from Centocor located in Malvern, Pa.). Examples of antimitotic agents include methotrexate, azathioprine, vincristine, vinblastine, fluorouracil, adriamycin, and mutamycin.

Examples of cytostatic or antiproliferative agents include angiopeptin (a somatostatin analog from Ibsen located in the United Kingdom), angiotensin converting enzyme inhibitors such as CAPTOPRIL (available from Squibb located in New York, N.Y.), CWLAZAPRIL (available from Hoffman-LaRoche located in Basel, Switzerland), or LISINOPRIL (available from Merck located in Whitehouse Station, N.J.), calcium channel blockers (such as nifedipine), colchicine, fibroblast growth factor (FGF) antagonists, fish oil (omega 3-fatty acid), histamine antagonists, LOVASTATIN (an inhibitor of HMG-CoA reductase, a cholesterol lowering drug from Merck), methotrexate, monoclonal antibodies [such as platelet-derived growth factor (PDGF) receptors], nitroprusside, phosphodiesterase inhibitors, prostaglandin inhibitor (available from GlaxoSmithKline located in United Kingdom), seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other types of drugs may be developed which are equally applicable for use with the present invention. The treatment of diseases using the above therapeutic agents are known in the art. The calculation of dosages, dosage rates and appropriate duration of treatment are previously known in the art. Furthermore, the drugs or agents are loaded at desired concentration levels per methods well known in the art to render the device ready for implantation.

In use, the drug-eluting medical device is deployed using conventional techniques. Once in position, the drug gradually diffuses into adjacent tissue at a rate dictated by the parameters associated with any polymer coat layer. The total dosage that is delivered is limited by the total amount of the drug that had been loaded within the porous medical device. The drug is selected to treat the deployment site and/or locations downstream thereof. For example, deployment in the carotid artery will serve to deliver such drug to the brain.

In another embodiment, the present invention includes a method of making tube stock for subsequent fabrication into a medical device. The method includes providing a biocompatible material as heretofore described. Modifications to the primary components (e.g., thermally controlled chamber, die, etc.) of the high speed injection molding apparatus may be made as discussed herein so that such components are able to withstand the higher temperature requirements imposed by use of relatively high melting point temperature metals or metal alloys. The biocompatible material is high speed injection molded as discussed herein using modified high speed injection molding process and apparatus known or to be developed by those in the metallurgical arts so as to form near net shape tube stock. Appropriate post-processing steps may be applied to the newly formed tube stock as needed in order to further refine the mechanical and physical properties of the material.

Various medical devices and tube stock can be made according to another-process known as semi-solid (slurry-based) die casting, which is related to the process of high speed injection molding. Existing apparatus used in conjunction with the semi-solid die casting process for processing aluminum based alloys (FIG. 2) may be adapted for use with higher temperature biocompatible materials. An embodiment of the present invention includes a method of making a medical device by semi-solid die casting. The method includes providing a suitable biocompatible material to form the body of the medical device. Examples of suitable biocompatible materials that can be used in accordance with the present invention include iron-carbon, cobalt based superalloys, cobalt-chromium, tantalum, titanium, nickel-titanium, niobium, niobium-vanadium, niobium-zirconium, niobium-tantalum-zirconium, titanium-tantalum, tantalum-titanium, niobium-tantalum, tantalum-niobium, niobium-titanium, titanium-niobium, tantalum-tungsten, tantalum-tungsten-hafnium, palladium-silver, silver-palladium, and platinum-iridium. Each of these particular types of alloys generally has a high melting point temperature as set forth in Table 1.

The process of semi-solid die casting is then applied to the biocompatible material for subsequent formation of a net shape medical device or tube stock, wire or the like. In particular, the material is processed into a semi-solid slurry suspension while being retained in a thermally controlled chamber. The semi-solid slurry suspension is processed by heating the material to a temperature above the material's solidus temperature, yet below the material's liquidus temperature. As with high speed injection molding, modifications to the primary components (e.g., thermally controlled chamber, die casting device, etc.) of the semi-solid die casting apparatus can be made so that such components are able to accommodate the higher temperatures of any suitable metals or metal alloys used in accordance with the invention.

While the semi-solid slurry suspension is being maintained in the thermally controlled chamber, a shearing force is applied to the slurry suspension. The shearing force is applied to inhibit the formation of dendritic structures during solidification and create rounded solid particles in the semi-solid slurry suspension. Shearing forces can be applied by techniques known or to be developed, such as mechanical and electromagnetic forces. Thus, the semi-solid state can be characterized as a suspension of rounded solid-phase particles in a liquid matrix. The solid portion of the slurry suspension should be uniformly distributed throughout the mixture. This is accomplished by the shearing force applied to the slurry suspension.

After the semi-solid slurry suspension has reached a desired viscosity, the suspension is transferred to a die casting device for the subsequent formation of the medical device. The semi-solid slurry suspension can be transferred by various mechanisms that include gravity, mechanical, vacuum, and the like, while being simultaneously maintained in a thermally controlled environment during the transfer.

The semi-solid slurry suspension is cast into the die to form the medical device while being maintained at a temperature in the equilibrium state (i.e., between the solidus and liquidus phase), which is dependant on the particular melting point temperature material being used. As the semi-solid slurry suspension cools within the die (or subjected to a cooling process), the material begins to solidify and forms the body of the medical device. As a result, the newly formed medical device can be removed from the die after it has solidified. It may be necessary to apply post-processing to the medical device to further define its mechanical and physical features.

In an alternative embodiment, a medical device made by semi-solid (slurry-based) die casting of the previous embodiment can be made porous for subsequent impregnation with a drug. The process of semi-solid die casting is applied in the same manner to the high melting point temperature metal or metal alloy, except that a binder is mixed into the slurry suspension while being maintained in a semi-solid slurry suspension. The mixture is then cast into the die. The binder is removable through post-processing, which is described in greater detail herein.

The present invention also provides a method of making tube stock using the process of semi-solid (slurry-based) die casting. Semi-solid die casting is applied in the same manner as for the manufacture of near net shape medical devices described herein. Following the formation of tube stock, appropriate post-processing steps can be applied. The tube stock may be subsequently formed into a stent or other medical device.

In addition to the various methods of making medical devices and tube stock using one of the processes of high speed injection molding and semi-solid die casting set forth above, the present invention also provides a medical device for use in treating a human patient. The medical device includes a net shape biocompatible material formed by at least one of the processes of high speed injection molding and semi-solid die casting. Possible materials used as the biocompatible material are the same as those set forth herein with each having a relatively high melting point temperature.

Figures 6, 7:
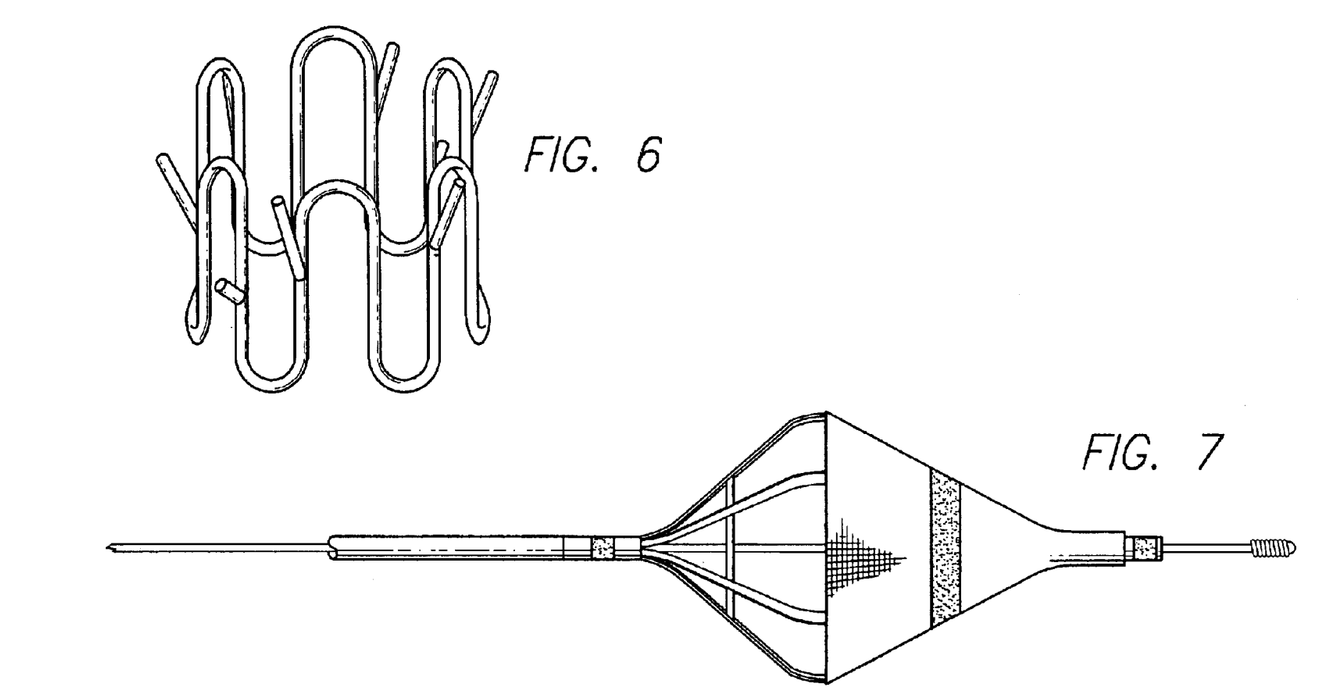
FIG. 6 is a perspective view of an anastomosis device made in accordance with the present invention.
FIG. 7 is a longitudinal plan view of an embolic protection device in an expanded condition made in accordance with the present invention.
Figure 8:
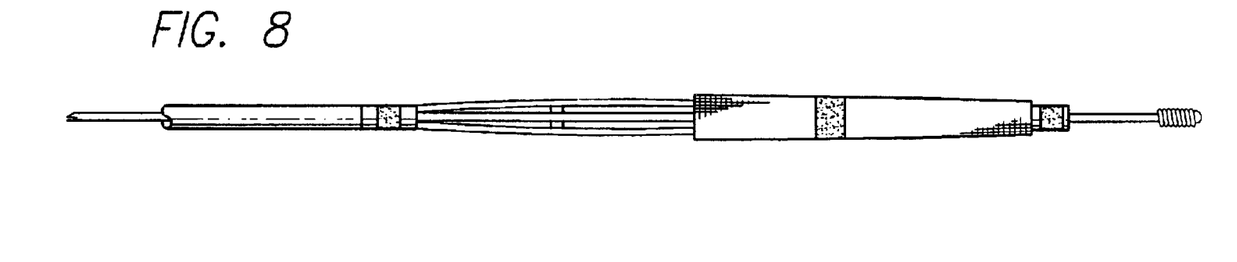
FIG. 8 is longitudinal plan view of an embolic protection device in an unexpanded condition made in accordance with the present invention.
Figure 9:
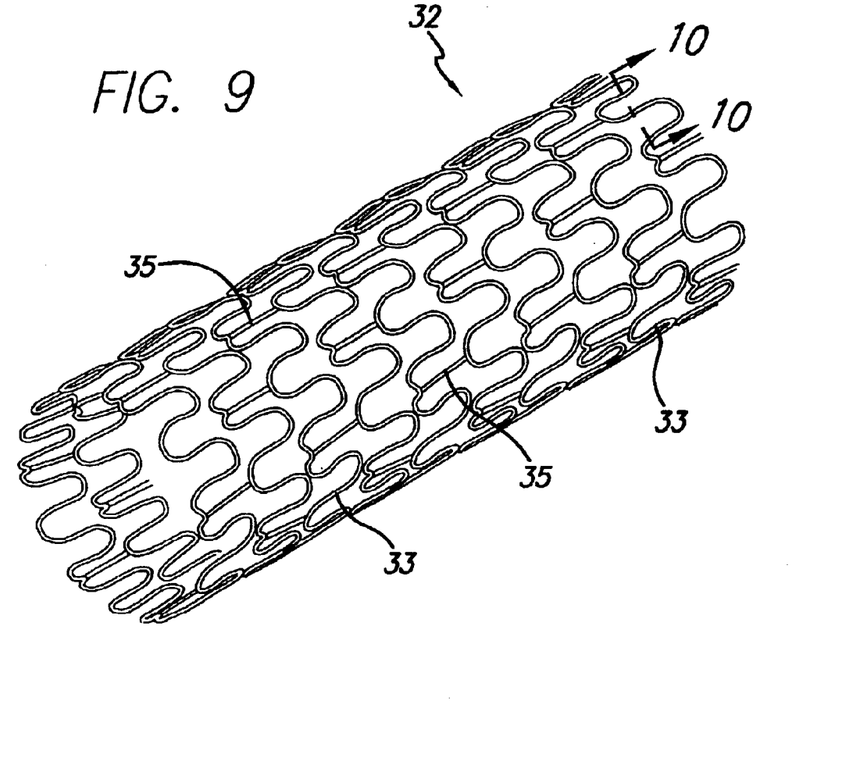
FIG. 9 is a perspective view of a stent made in accordance with the present invention.
Figure 10:
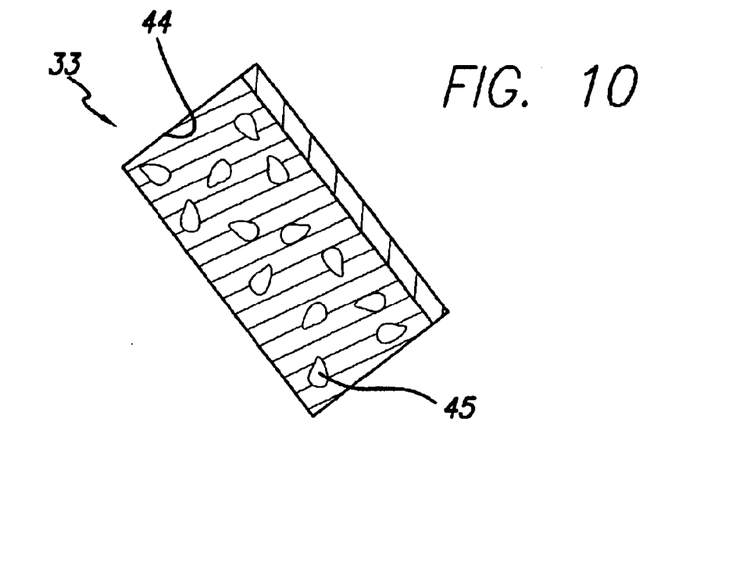
FIG. 10 is a cross-sectional view along the lines 10—10 of FIG. 9.
Figure 11:
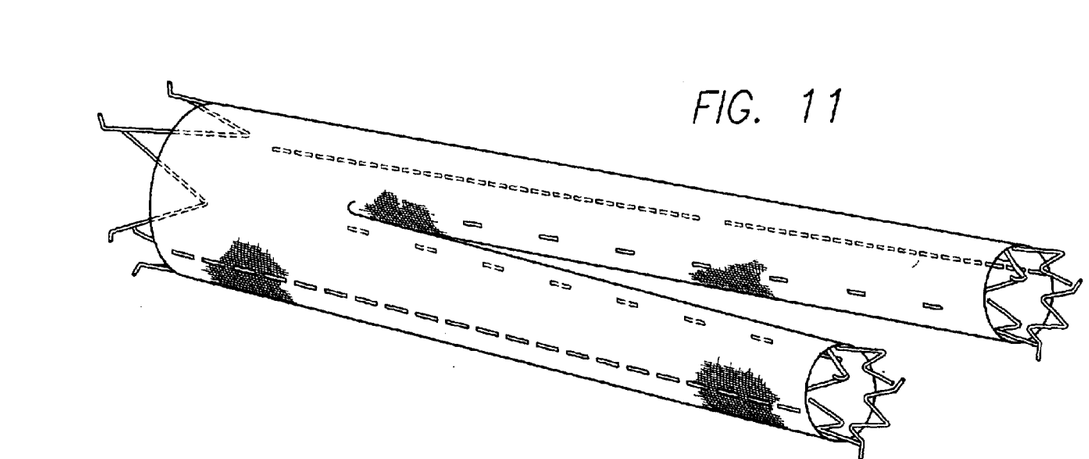
FIG. 11 is a perspective view of a graft assembly having attachment systems made in accordance with the present invention.

As shown in FIGS. 3–12, many types of medical devices may be made in accordance with the present invention. In one embodiment, the medical device is an intravascular device such as a stent (FIGS. 9 and 10). Consistent with the present invention, the stent may be formed from a biocompatible material 44 that may be formed with interconnected or discrete pores or voids 45 (FIG. 10). In alternative embodiments, the medical device can be part of an embolic protection device (FIGS. 7 and 8), an attachment system for an endovascular graft (FIG. 11), a guide wire, a wire lead, a catheter (FIGS. 4 and 5), a pacemaker lead end, and an anastomosis device (FIG. 6).

Figure 3:
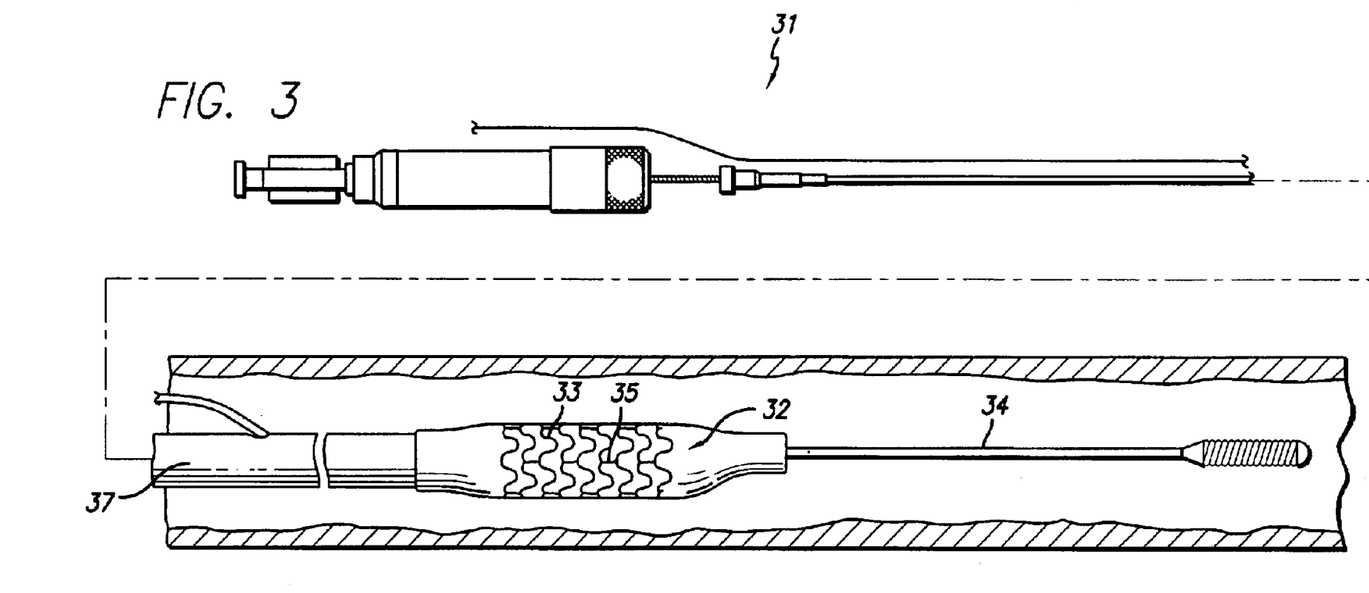
FIG. 3 is an elevational view, partially in section, of a catheter-stent assembly with the stent and accompanying guide wire made in accordance with the present invention.
Figure 4:
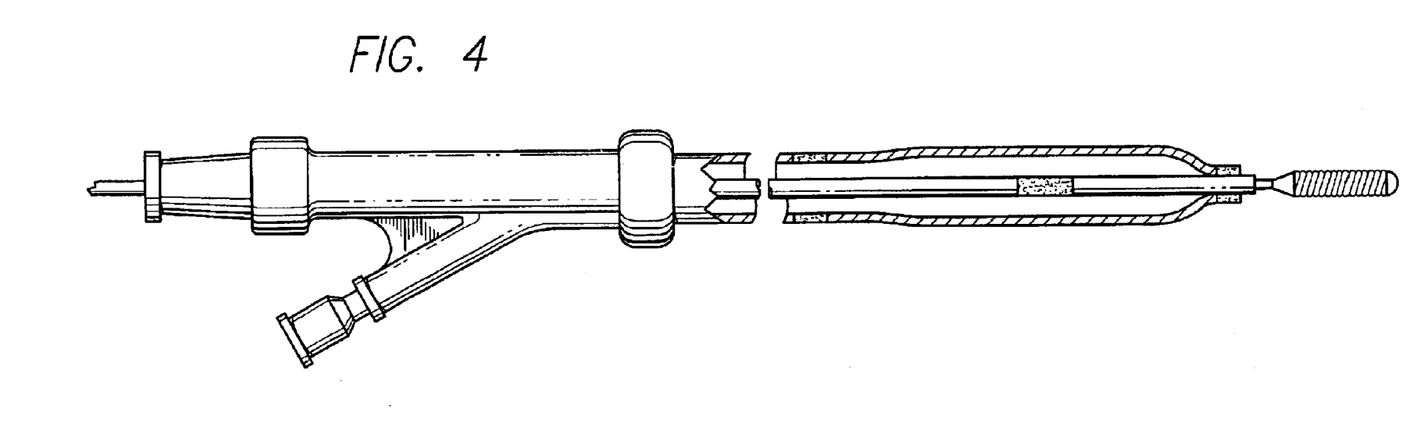
FIG. 4 is a longitudinal plan view in partial cross-section of an over-the-wire intravascular catheter assembly made in accordance with the present invention.
Figure 5:
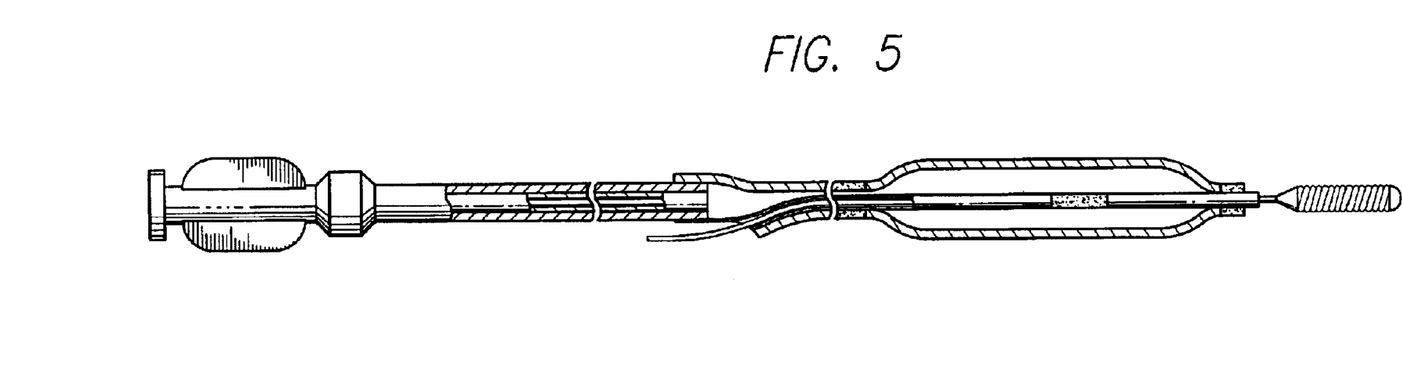
FIG. 5 is a longitudinal plan view in partial cross-section of a rapid exchange intravascular catheter assembly made in accordance with the present invention.

With further reference to the drawings, and particularly FIG. 3, a catheter-stent assembly 31 with a stent 32, catheter 37 and guide wire 34 being made in accordance with the invention is shown. Stents are well known in the art and can have many different types of patterns and configurations. The stent shown in FIG. 3 represents a typical stent pattern made from stainless steel tubing. Other patterns are well known in the art, and the foregoing description of a stent and delivery system is by way of example, and is not meant to be limiting.

The present invention further provides tube stock for subsequent use as a medical device such as a stent. Tube stock of the invention includes an elongated body having at least a portion thereof constructed of a biocompatible material formed by at least one of the processes of high speed injection molding and semi-solid die casting. Possible materials for use as the biocompatible material are the same as those set forth herein (see Table 1). Additional post-processing may be applied to the tube stock in order to form a desired medical device.

Regarding the application of post-processing steps to the newly formed medical device or tube stock, the device or tube can be subjected to mechanical processing in order to develop desired mechanical properties. Such post-processing steps that may be used to develop the desired mechanical properties include exerting high mechanical pressures, s waging, tempering and hardening. The outer diameter and/or the inner diameter of the tube stock can be machined to size after being removed from the die so as to size the tube to a desired specification. The tube stock can also be reamed to size if desired. The tube stock can also be ground or drawn to final size.

Additional post-processing steps to reach the desired mechanical properties can include processing a non-porous medical device in a traveling ring furnace where the material is melted and re-solidified as the ring travels down the length of the device, and processing the device under high mechanical pressure in a vacuum to sinter grains of the device together. In order to finish a coated medical device to desired dimensions, the outer diameter of the device can be post processed through centerless grinding or drawing to reduce the coating thickness. The inner diameter can be bored to improve both dimensions and surface roughness.

The illustrative stent 32 of the present invention and similar medical device structures can be made in many ways. One method of making such a stent is to cut tube stock or sheets of biocompatible material formed according to the method and devices of the present invention so as to remove portions of the tube stock in the desired pattern for the stent, leaving relatively untouched the portions of the tube stock that are to form, for example, the cylindrical rings 33 and links 35. Since the finished product stent diameter is very small, the tubing from which the medical device is made must necessarily also have a small diameter. Typically, the tube stock or sheet from which the medical device is made has an outer diameter in the range of about 0.03 inch (1.0 mm) to about 0.5 inch (13.0 mm) in the unexpanded condition, and can be expanded to an outer diameter of about 0.1 inch (2.5 mm) or more. The wall thickness of the tubing is typically in the range of about 0.002 (0.05 mm) to 0.01 inch (0.25 mm). Various processes of forming the desired stent pattern are available and are known in the art, such as, but not limited to, using laser or chemical etching, electronic discharge machining and stamping. As with the foregoing stent dimensions, all of the medical devices that can be formed utilizing the present invention can vary substantially in size and shape so that the disclosed dimensions and shapes are representative examples only and are not meant to be limiting.

Figure 12:
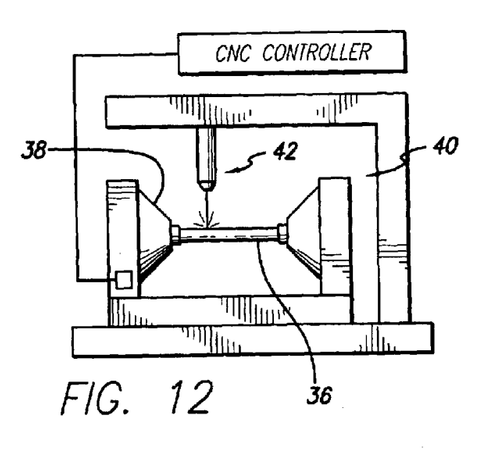
FIG. 12 is a schematic representation of equipment for laser cutting tubing in the manufacture of stents and anastomosis clips, in accordance with the present invention.

After forming the tube stock using either the high speed injection molding process or the semi-solid die casting process of the present invention, the tube stock 36 may be cut in the desired pattern by using a machine-controlled laser, as illustrated schematically in FIG. 12 and as is well known in the art. The tube stock may put in a rotatable collet fixture 38 of a machine-controlled apparatus 40 for positioning the tube stock relative to a machine-controlled laser 42, utilizing a computerized numeric controller (CNC). According to machine-encoded instructions, the tubing is rotated and moved longitudinally relative to the laser. The laser selectively removes material from the tube stock by ablation, and a desired pattern is cut into the tube stock.

Cutting a fine structure via a machine-controlled laser requires minimal heat input and the ability to manipulate the tube stock with precision. It is also necessary to support the tube stock, yet not allow the tube stock to distort during the cutting operation. In one embodiment of the present invention, the tube stock is made of stainless steel with an outside diameter having a range of about 0.04 inch (1.02 mm) to about 0.4 inch (10.2 mm) and a wall thickness of about 0.002 inch (0.05 mm) to about 0.01 inch (0.25 mm). To achieve a relatively small geometry of a desired stent pattern formed with ring struts 33 and links 35 having a width of about 0.0035 inch (0.089 mm), it is necessary to have very precise control of the laser's power level, focused spot size and positioning of the laser cutting path, which is well known in the art. After laser cutting, the near-net shape stent may be surface modified.

The foregoing laser cutting process to form the cylindrical rings 33 can be used with stainless steel and metals such as cobalt-chromium, titanium, tantalum, platinum, nickel-titanium, and alloys thereof, and other biocompatible metals disclosed herein that are suitable for use in humans, and typically used for intravascular stents. Further, while the formation of the cylindrical rings is described above, other processes of forming the rings are possible and are known in the art, such as by using chemical etching, electronic discharge machining, stamping, and other processes.

While particular forms of the invention have been illustrated and described, it will also be apparent to those skilled in the art that various modifications and improvements can be made without departing from the spirit and scope of the invention. More specifically, it should be clear that the present invention is not limited to the medical devices described herein, and may be used to form various other types of medical devices. Accordingly, it is not intended that the invention be limited, except as by appended claims.

What is claimed:

1. A method of making a medical device, comprising:

providing a biocompatible material;

casting a porous medical device from the biocompatible material by processing the biocompatible material into a thixotropic state; and impregnating the medical device with a drug wherein a binder material is injected into the thixotropic material in order to cast the porous medical device.

2. The method of claim 1, wherein forming a porous medical device further comprises:

processing the biocompatible material into a semi-solid thixotropic state while the material is maintained in a thermally controlled chamber;

applying a shearing action to the biocompatible material in the semi-solid thixotropic state while the material is in the thermally controlled chamber, high speed injecting the semi-solid thixotropic biocompatible material into a die;

injecting the binder material into the semi-solid thixotropic material;

solidifying the binder material and the semi-solid thixotropic material to form a medical device;

removing the medical device from the die; and removing the binder material from the medical device.

3. The method of claim 2, wherein injecting a binder material into the semi-solid thixotropic material includes using a binder material selected from the group consisting of polysilazine, unsaturated polymer resin, bisphenoic unsaturated polymer resin, thermoplastic polymer, polycarbonate and colloidal silica.

4. The method of claim 1, wherein impregnating the medical device with a drug includes using a drug comprising at least one of antiplatelets, anticoagulants, antifibrins, anti-inflammatories, antithrombins, and antiproliferatives.

* * * * *

UNITED STATES PATENT AND TRADEMARK OFFICE
CERTIFICATE OF CORRECTION

PATENT NO.      : 6,725,901 B1
DATED           : April 27, 2004
INVENTOR(S)     : Pamela A. Kramer and James M. Carlson It is certified that error appears in the above-identified patent and that said Letters Patent is hereby corrected as shown below:

Column 3,
Line 40, delete "stent-having" and insert -- stent having --.

Column 8,
Line 67, after "art" insert -- . --.

Column 9,
Line 31, delete "CWLAZAPRIL" and insert -- CILAZAPRIL --.

Column 12,
Line 21, delete "s waging" and insert -- swaging --.

Signed and Sealed this

Twenty-first Day of December, 2004

JON W. DUDAS
*Director of the United States Patent and Trademark Office*